US010213325B2

(12) United States Patent
Halldorsson (10) Patent No.: US 10,213,325 B2
(45) Date of Patent: Feb. 26, 2019

(54) SUSPENSION LINER WITH SEAL COMPONENT (71) Applicant: Ossur HF, Reykjavik (IS)

(72) Inventor: Olafur Freyr Halldorsson, Reykjavik (IS)

(73) Assignee: OSSUR HF, Reykjavik (IS)

( * ) Notice: Subject to any disclaimer, the term of this patent is extended or adjusted under 35 U.S.C. 154(b) by 0 days.

(21) Appl. No.: 15/428,427

(22) Filed: Feb. 9, 2017

(65) Prior Publication Data
US 2017/0151073 A1    Jun. 1, 2017

Related U.S. Application Data (63) Continuation of application No. 14/615,938, filed on Feb. 6, 2015, now Pat. No. 9,566,175, which is a continuation of application No. 13/589,415, filed on Aug. 20, 2012, now Pat. No. 8,956,422.

(60) Provisional application No. 61/526,035, filed on Aug. 22, 2011.

(51) Int. Cl.
A61F 2/78    (2006.01)
A61F 2/80    (2006.01)

(52) U.S. Cl.
CPC ...... *A61F 2/7812* (2013.01); *A61F 2002/785* (2013.01); *A61F 2002/7818* (2013.01); *A61F 2002/802* (2013.01); *F04C 2270/0421* (2013.01)

(58) Field of Classification Search
CPC ....... A61F 2/78; A61F 2/80; A61F 2002/7806
See application file for complete search history.

(56) References Cited

U.S. PATENT DOCUMENTS

| 980,457 A | 1/1911 | Toles |
|---|---|---|
| 1,398,824 A | 11/1921 | Abrams |
| 1,893,853 A | 1/1933 | Tullis |

(Continued)

FOREIGN PATENT DOCUMENTS

| AT | 369 978 B | 2/1983 |
|---|---|---|
| DE | 484 363 C | 10/1929 |

(Continued)

OTHER PUBLICATIONS

International Search Report from PCT Application No. PCT/US2017/029063, dated Jul. 21, 2017.

(Continued)

*Primary Examiner* — Bruce E Snow
(74) *Attorney, Agent, or Firm* — Workman Nydegger (57) ABSTRACT A suspension liner is provided for use as an interface between a residual limb and a prosthetic socket. The liner has an elongate, generally conical liner body formed from at least one material segment that is at least radially elastically extensible from a relaxed non-extended condition and including proximal and distal end areas, and a seal component connected to the liner body and having an exterior surface defining at least one exterior seal protruding from the exterior surface and extending radially outwardly from the seal component relative to a longitudinal axis of the liner body. The at least one interior seal is located along an interior surface of the seal component and defines at least one blade extending obliquely toward the liner body. A portion of the seal component carrying the interior seal extends freely and is movable relative to the liner body.

16 Claims, 4 Drawing Sheets

(56) References Cited

U.S. PATENT DOCUMENTS

| | | |
|---|---|---|
| 2,325,656 A | 8/1943 | Brophy |
| 2,464,443 A | 3/1949 | Ganoe et al. |
| 2,530,285 A | 11/1950 | Catranis |
| 2,533,404 A | 12/1950 | Sharp et al. |
| 2,634,424 A | 4/1953 | O'Gorman |
| 2,671,225 A | 3/1954 | Schoene et al. |
| 2,689,351 A | 9/1954 | Schindler |
| 2,808,593 A | 10/1957 | Andersen |
| 3,393,407 A | 7/1968 | Kandel |
| 3,587,572 A | 6/1971 | Evans |
| 3,671,980 A | 6/1972 | Baird |
| 3,947,897 A | 4/1976 | Owens |
| 4,128,903 A | 12/1978 | Marsh et al. |
| 4,215,679 A | 8/1980 | Rustin |
| 4,311,317 A | 1/1982 | Bartels |
| 4,319,413 A | 3/1982 | Mattil |
| 4,347,204 A | 8/1982 | Takagi et al. |
| 4,474,573 A | 10/1984 | Detty |
| 4,635,626 A | 1/1987 | Lerman |
| 4,738,249 A | 4/1988 | Linman et al. |
| 4,767,735 A | 8/1988 | Ewen et al. |
| 4,885,828 A | 12/1989 | Kozlowski |
| 4,908,037 A | 3/1990 | Ross |
| 4,923,474 A | 5/1990 | Klasson et al. |
| 5,007,937 A | 4/1991 | Fishman et al. |
| 5,055,528 A | 10/1991 | Kioka et al. |
| 5,122,583 A | 6/1992 | Ewen et al. |
| 5,139,523 A | 8/1992 | Paton et al. |
| 5,163,965 A | 11/1992 | Rasmusson et al. |
| 5,169,161 A | 12/1992 | Jones |
| 5,226,918 A | 7/1993 | Silagy et al. |
| 5,244,716 A | 9/1993 | Thornton et al. |
| 5,314,496 A | 5/1994 | Harris et al. |
| 5,376,129 A | 12/1994 | Faulkner et al. |
| 5,376,131 A | 12/1994 | Lenze et al. |
| 5,387,245 A | 2/1995 | Fay et al. |
| 5,549,709 A | 8/1996 | Caspers |
| 5,571,208 A | 11/1996 | Caspers |
| 5,571,209 A | 11/1996 | Brown, Sr. |
| 5,593,454 A | 1/1997 | Helmy |
| 5,658,353 A | 8/1997 | Layton |
| 5,702,489 A | 12/1997 | Slemker |
| 5,718,925 A | 2/1998 | Kristinsson et al. |
| 5,728,168 A | 3/1998 | Laghi et al. |
| 5,728,170 A | 3/1998 | Becker et al. |
| 5,735,906 A | 4/1998 | Caspers |
| 5,830,237 A | 11/1998 | Kania |
| 5,885,674 A | 3/1999 | Maemoto et al. |
| 5,888,216 A | 3/1999 | Haberman |
| 5,888,230 A | 3/1999 | Helmy |
| 5,904,722 A | 5/1999 | Caspers |
| 5,931,872 A | 8/1999 | Lohmann |
| 5,972,036 A | 10/1999 | Kristinsson et al. |
| 5,980,577 A | 11/1999 | Radis et al. |
| 6,076,284 A | 6/2000 | Terlizzi |
| 6,136,039 A | 10/2000 | Kristinsson et al. |
| 6,149,691 A | 11/2000 | Fay et al. |
| 6,171,431 B1 | 1/2001 | Gallagher, Jr. et al. |
| 6,231,616 B1 | 5/2001 | Helmy |
| 6,231,617 B1 | 5/2001 | Fay |
| 6,273,918 B1 | 8/2001 | Yuhasz et al. |
| 6,287,345 B1 | 9/2001 | Slemker et al. |
| 6,361,568 B1 | 3/2002 | Hoerner |
| 6,368,357 B1 | 4/2002 | Schon et al. |
| 6,406,499 B1 | 6/2002 | Kania |
| 6,468,938 B1 | 10/2002 | Govoni et al. |
| 6,485,776 B2 | 11/2002 | Janusson et al. |
| 6,508,842 B1 | 1/2003 | Caspers |
| 6,544,292 B1 | 4/2003 | Laghi |
| 6,554,868 B1 | 4/2003 | Caspers |
| 6,585,774 B2 | 7/2003 | Dean, Jr. et al. |
| 6,626,952 B2 | 9/2003 | Janusson et al. |
| 6,645,253 B2 | 11/2003 | Caspers |
| 6,706,364 B2 | 3/2004 | Janusson et al. |
| 6,726,726 B2 | 4/2004 | Gaspers |
| 6,761,742 B2 | 7/2004 | Caspers |
| 6,852,269 B2 | 2/2005 | Eberle et al. |
| 6,926,742 B2 | 8/2005 | Caspers et al. |
| 6,929,125 B1 | 8/2005 | Seamans |
| 6,964,688 B1 | 11/2005 | Kania |
| 7,001,563 B2 | 2/2006 | Janusson et al. |
| 7,025,793 B2 | 4/2006 | Egilsson |
| 7,118,602 B2 * | 10/2006 | Bjarnason ............ A61F 2/7812 623/32 |
| 7,144,429 B2 | 12/2006 | Carstens |
| 7,169,188 B2 | 1/2007 | Carstens |
| 7,169,189 B2 | 1/2007 | Bjarnason et al. |
| 7,235,108 B2 | 6/2007 | Carstens |
| 7,291,182 B1 | 11/2007 | Kania |
| 7,351,264 B2 | 4/2008 | Wilson |
| 7,427,297 B2 | 9/2008 | Patterson et al. |
| 7,592,286 B2 | 9/2009 | Morini et al. |
| 7,749,281 B2 | 7/2010 | Egilsson |
| 7,771,487 B2 | 8/2010 | Mantelmacher |
| 7,909,884 B2 | 3/2011 | Egilsson et al. |
| 8,034,120 B2 | 10/2011 | Egilsson et al. |
| 8,052,760 B2 | 11/2011 | Egilsson et al. |
| 8,097,043 B2 | 1/2012 | Egilsson |
| 8,206,459 B1 | 6/2012 | Lock et al. |
| 8,372,159 B2 | 2/2013 | MacKenzie |
| 8,956,422 B2 * | 2/2015 | Halldorsson ......... A61F 2/7812 623/36 |
| 9,603,726 B2 | 3/2017 | Egilsson et al. |
| 9,707,106 B2 | 7/2017 | Egilsson et al. |
| 2001/0005798 A1 | 6/2001 | Caspers |
| 2001/0016781 A1 | 8/2001 | Caspers |
| 2002/0040248 A1 | 4/2002 | Karason |
| 2002/0087215 A1 | 7/2002 | Caspers |
| 2002/0091449 A1 | 7/2002 | Caspers et al. |
| 2002/0099450 A1 | 7/2002 | Dean, Jr. et al. |
| 2002/0165619 A1 | 11/2002 | Hellberg |
| 2002/0183859 A1 | 12/2002 | Houser |
| 2003/0181989 A1 | 9/2003 | Eberle et al. |
| 2003/0191539 A1 | 10/2003 | Caspers |
| 2004/0024322 A1 | 2/2004 | Caspers |
| 2004/0030411 A1 | 2/2004 | Caspers |
| 2004/0040248 A1 | 3/2004 | Vilnes |
| 2004/0098136 A1 | 5/2004 | Caspers |
| 2004/0122528 A1 | 6/2004 | Egilsson |
| 2004/0143345 A1 | 7/2004 | Caspers |
| 2004/0167638 A1 | 8/2004 | Caspers |
| 2004/0181290 A1 | 9/2004 | Caspers |
| 2004/0236434 A1 | 11/2004 | Carstens |
| 2004/0243251 A1 | 12/2004 | Carstens |
| 2004/0243252 A1 | 12/2004 | Carstens |
| 2005/0101693 A1 | 5/2005 | Arbogast et al. |
| 2005/0216095 A1 | 9/2005 | Egilsson |
| 2005/0240282 A1 | 10/2005 | Rush et al. |
| 2005/0240283 A1 | 10/2005 | Kania |
| 2005/0267598 A1 | 12/2005 | Bjarnason et al. |
| 2005/0267599 A1 | 12/2005 | Bjarnason |
| 2006/0212128 A1 | 9/2006 | Nachbar |
| 2006/0293762 A1 | 12/2006 | Schulman et al. |
| 2007/0005149 A1 | 1/2007 | Egilsson et al. |
| 2007/0021295 A1 | 1/2007 | Morini et al. |
| 2007/0027556 A1 | 2/2007 | Wilson |
| 2007/0043450 A1 | 2/2007 | Pickering et al. |
| 2007/0061017 A1 | 3/2007 | Wilson |
| 2007/0123998 A1 * | 5/2007 | Egilsson ............... A61F 2/7812 623/36 |
| 2007/0179606 A1 | 8/2007 | Huyghe et al. |
| 2008/0086218 A1 | 4/2008 | Egilsson |
| 2008/0147202 A1 | 6/2008 | Danzig et al. |
| 2008/0188949 A1 | 8/2008 | MacKenzie |
| 2008/0221705 A1 | 9/2008 | Scussel |
| 2008/0221706 A1 | 9/2008 | Scussel et al. |
| 2008/0269914 A1 | 10/2008 | Coppens et al. |
| 2009/0036999 A1 | 2/2009 | Egilsson et al. |
| 2009/0069171 A1 | 3/2009 | Sagae |
| 2009/0157196 A1 | 6/2009 | Danzig et al. |
| 2009/0182435 A1 | 7/2009 | Haberman |
| 2009/0198346 A1 | 8/2009 | Perkins et al. |
| 2009/0240344 A1 | 9/2009 | Colvin et al. |
| 2009/0306791 A1 | 12/2009 | Slemker et al. |

(56) References Cited

U.S. PATENT DOCUMENTS

| | | |
|---|---|---|
| 2010/0070051 A1 | 3/2010 | Carstens |
| 2010/0185300 A1 | 7/2010 | MacKenzie |
| 2010/0249950 A1 | 9/2010 | Bielefeld |
| 2010/0274364 A1 | 10/2010 | Pacanowsky et al. |
| 2010/0318196 A1 | 12/2010 | Egilsson |
| 2011/0029096 A1 | 2/2011 | Laghi |
| 2011/0035027 A1 | 2/2011 | McCarthy |
| 2011/0054635 A1 | 3/2011 | Watts |
| 2011/0071649 A1 | 3/2011 | McKinney |
| 2011/0077748 A1 | 3/2011 | Egilsson et al. |
| 2011/0118854 A1 | 5/2011 | Halldorsson |
| 2012/0041568 A1 | 2/2012 | MacKenzie |
| 2012/0095571 A1 | 4/2012 | Gunnarsson et al. |
| 2013/0053982 A1 | 2/2013 | Halldorsson |
| 2013/0138224 A1 | 5/2013 | MacKenzie |
| 2013/0197670 A1 | 8/2013 | MacKenzie |
| 2013/0331952 A1 | 12/2013 | Halldorsson et al. |
| 2015/0142133 A1 | 5/2015 | Egilsson et al. |
| 2017/0105853 A1 | 4/2017 | Jonsson et al. |
| 2017/0304085 A1 | 10/2017 | Kurth |

FOREIGN PATENT DOCUMENTS

| | | |
|---|---|---|
| DE | 745 981 C | 5/1944 |
| DE | 813 190 C | 9/1951 |
| DE | 1 795 809 U | 9/1959 |
| DE | 2 060 239 A1 | 6/1972 |
| DE | 2 127 269 A1 | 12/1972 |
| DE | 2 540 138 A1 | 3/1977 |
| DE | 2 544 446 A1 | 4/1977 |
| DE | 3 221 920 A1 | 4/1983 |
| DE | 3 508 919 A1 | 9/1986 |
| DE | 9 419 208 U1 | 1/1995 |
| EP | 0 631 765 A1 | 1/1995 |
| EP | 1 572 043 A2 | 9/2005 |
| EP | 2353550 A1 | 8/2011 |
| EP | 2745807 A1 | 6/2014 |
| EP | 2815728 A1 | 12/2014 |
| FR | 2 420 335 A1 | 10/1979 |
| FR | 2 539 616 A1 | 7/1984 |
| FR | 2 828 093 A1 | 2/2003 |
| GB | 263 377 A | 12/1926 |
| GB | 267 988 A | 3/1927 |
| GB | 826 041 A | 12/1959 |
| GB | 2 069 847 A | 9/1981 |
| GB | 2 087 727 A | 6/1982 |
| JP | H0623406 A | 2/1994 |
| JP | H07109314 A | 4/1995 |
| JP | H7-155343 A | 6/1995 |
| JP | H9-104714 A | 4/1997 |
| JP | 2637076 B2 | 8/1997 |
| JP | 2740503 B2 | 4/1998 |
| JP | H10-182740 A | 7/1998 |
| JP | 2001-055413 A | 2/2001 |
| JP | 2002-500697 A | 1/2002 |
| JP | 2006-176565 A | 7/2006 |
| JP | 2006-316160 A | 11/2006 |
| JP | 2006-528271 A | 12/2006 |
| JP | 3984304 B2 | 10/2007 |
| WO | 97/34548 A2 | 9/1997 |
| WO | 9734548 A2 | 9/1997 |
| WO | 00/74611 A2 | 12/2000 |
| WO | 01/54631 A1 | 8/2001 |
| WO | 01/67842 A1 | 9/2001 |
| WO | 02/26158 A2 | 4/2002 |
| WO | 03/024367 A2 | 3/2003 |
| WO | 03/024370 A1 | 3/2003 |
| WO | 03/039398 A2 | 5/2003 |
| WO | 03/099173 A1 | 12/2003 |
| WO | 2004/060136 A2 | 7/2004 |
| WO | 2010/085336 A1 | 7/2010 |
| WO | 2013/005735 A1 | 1/2013 |
| WO | 2015073793 A1 | 5/2015 |

OTHER PUBLICATIONS

"Silicone-Only Suspension (SOS) with Socket-Loc and the Ring for the Lower Limb", found at, http://www.oandp.org/ipo/library/1995_01_002.asp. Journal of Prosthetics and Orthotics 1995; vol. 7, No. 1, p. 2.

Iceross Comfort Locking/Cushion Product Information Brochure, Mar. 27, 2009, 3 Pages.

Iceross Dermo, Product Information Sheets from Internet, http://www.ossur.com/prosthetics/liners/dermo, Mar. 27, 2009, 2 Sheets.

Military inStep: Prosthetic Socks and Liners, Product Information Sheets from Internet, http://www.amputee-coalition.org/military-instep/prosthetic-socks, Mar. 27, 2009, 3 Pages.

Prosthetic & Orthotic Update NewsLetter, No. 32, Internet Search Conducted Mar. 27, 2009, 4 Pages.

Walopur Platilon U, Product Information Brochure of Epurex Films GmbH & Co., KG, Internet Search Result conducted Mar. 27, 2009, 2 Pages.

International Search Report and Written Opinion Issued in PCT/US2012/051645, dated Dec. 3, 2012.

Supplementary EP Search Report from EP Application No. 07837275.2, dated Feb. 19, 2014, 6 pages.

Extended European Search Report from EP Application No. 14161004.8, dated May 22, 2014, 6 pages.

Extended European Search Report from Corresponding Application No. 14163512.8, dated Jul. 30, 2014.

ESP Opti-Seal, Product Installation Instructions, http://www.wearesp.com, Downloaded Dec. 12, 2014, 1 page.

ESP Opti-Seal, "The Most Versatile Suspension System Availiable", www.wearesp.com, Downloaded Dec. 12, 2014, 2 pages.

ESP Secure-Ring System (SRS), http://www.wearesp.com, Downloaded Dec. 12, 2014, 1 page.

ESP Secure-Ring System (SRS), Product Instructions Sheet, http://www.wearesp.com, downloaded Dec. 12, 2014, 2 pages.

International Search Report from PCT Application No. PCT/US2016/055269, dated Jan. 4, 2017.

Eshraghi et al., "Gait Biomechanics of Individuals with Transtibial Amputation: Effect of Suspension System," PLOS ONE, vol. 9, Issue. 5, May 2014, 12 Pages.

Eshraghi et al., "Pistoning Assessment in Lower Limb Prosthetic Sockets," Prosthetics and Orthotics International, vol. 36, No. 1, 2012, pp. 15-24.

Gholizadeh et al., "Transtibial Prosthesis Suspension Systems: Systematic Review of Literature," Clinical Biomechanics vol. 29, 2014, pp. 87-97.

"Slick SIL LSR," Surface Solutions Group LLC, retrieved from www.surfacesolutionsgroup.com on Mar. 30, 2017, 1 Page.

"Prosthetics Product Catalogue", Medi Prosthetics, www.medi-prosthetics.com, Jan. 2016, 184 pages.

"Verwendung und Verklebung Des LITE Vakuum-Ringes 5W700: Usage and Gluing of the 5W700 LITE Vacuum Ring," Wagner Polymertechnik GMBH, Sep. 6, 2016, 4 Pages.

* cited by examiner

SUSPENSION LINER WITH SEAL COMPONENT

CROSS-REFERENCE TO RELATED APPLICATION

This application claims priority to U.S. Ser. No. 14/615,938, filed Feb. 6, 2015, which claims priority to U.S. Ser. No. 13/589,415, filed Aug. 20, 2012, now U.S. Pat. No. 8,956,422, issued on Feb. 17, 2015, which claims the benefit of priority from U.S. Provisional Application Ser. No. 61/526,035, filed on Aug. 22, 2011, the entirety of which is incorporated by reference.

FIELD OF THE DISCLOSURE

This disclosure relates to a suspension liner for prosthetic devices, and more particularly to a suspension liner for enveloping a residual limb and having a seal component for engaging a prosthetic socket.

BACKGROUND

Suspension liner systems are widely used in prosthetic systems for residual limbs in order to stabilize soft tissue, minimize pistoning or stretching, assist circulation of the residual limb and add comfort.

Various solutions are found in the prior art, including those described in U.S. Pat. No. 7,025,793, granted on Apr. 11, 2006, and U.S. Pat. No. 8,034,120, granted on Oct. 11, 2011, both of which are incorporated herein by reference. According to these publications, a liner includes a liner body and a seal component located at the distal end area of the liner body. The seal component is flexible so it can conform to the shape of the residual limb and the internal wall of the prosthetic socket, thereby providing an airtight seal. The seal component minimizes movement of the limb within the socket, so as to prevent pistoning and rotation. In operation, the residual limb is stepped into the socket and expels air through a distal valve on the socket so as to create hypobaric suction below the seal component.

Some users find that known liners having sealing means fail to sufficiently tolerate volume fluctuations, and may leave pressure marks on the residual limb after periods of sustained use. Additional improvements may be required for some users in that known liners do not adequately conform to the user's anatomy, and therefore fail to provide necessary comfort and skin protection. Moreover, as with all suspension liners having sealing means, it is necessary that the liner provides reliable suspension after an initial phase of volume and shape conditioning after the liner is donned on the user's residual limb.

SUMMARY

A suspension liner with a seal component is described herein and provides a connection and interface between a prosthetic socket and residual limb. The connection is made by using a suspension liner with a seal so as to create a vacuum to suspend the residual limb to the socket. The suspension liner removes the need for a distal pin that is commonly employed in suspension liners and is used to couple to a hard, prosthetic socket and other prosthetic leg components. Moreover, because the seal is formed by the suspension liner itself, a sleeve of an exemplary type discussed in U.S. Pat. No. 6,592,539, granted Jul. 15, 2003 and incorporated herein by reference, is not required to seal the liner to the socket.

The suspension liner with a seal component has at least the benefits of mitigating distal pistoning from a distal pin. There is no restriction over the knee of the wearer to any sleeve. Therefore, the suspension liner with a seal component provides a reliable suspension without distal attachments or suspension sleeves.

Due to the particular liner and seal component embodiments discussed, herein the suspension liner provides a secure connection over varying residual limb volumes between the socket and the residual limb. Also, the liner and seal component embodiments provide a comfortable connection between the socket and the limb by reducing noticeable pressure marks.

According to an embodiment, the suspension liner includes an elongate, generally conical liner body formed from at least one material segment that is at least radially elastically extensible from a relaxed non-extended condition and including proximal and distal end areas, and a seal component connected to the liner body. The seal component has at least one exterior configuration for engaging a prosthetic socket and at least one interior configuration for movably engaging the liner body.

The exterior configuration may be arranged to have at least one seal that protrudes radially outwardly from an exterior surface of the seal component relative to a longitudinal axis of the liner body.

The interior configuration may be arranged to protrude inwardly toward the liner body, and may be yet further arranged to extend at an oblique angle relative to the longitudinal axis of the liner body. In a variation, the interior configuration defines at least one blade extending obliquely toward the liner body. The blade may taper toward its distal and proximal ends along a segment of the length of the liner body, such as tapering in thickness from an interior wall of the seal component toward the liner body exterior surface.

A portion of the seal component carrying the interior configuration extends freely and movable relative to the liner body.

In a variation of the interior configuration of the seal component, the seal component defines an inwardly pitched portion at the proximal end thereof and directed toward the liner body exterior surface.

In another variation, the interior configuration defines at least one blade extending toward the liner body with the blade being bounded by an outwardly pitched portion of the interior configuration located near a distal end of the seal component and an inwardly pitched portion at the proximal end of the seal component and directed toward the liner body exterior surface.

The seal component may define a base portion circumferentially secured to an exterior surface of the liner body. The base portion may have an attachment portion entirely secured to the exterior surface of the liner body, with the remainder of the seal component outside and proximally located relative to the attachment portion extending generally freely from the liner body.

The seal component may define a lip arranged against the liner body; the interior configuration may be located proximal relative to the lip. A clearance may be formed between the lip and an outwardly pitched portion of the interior configuration extending from a base portion located at a distal end of the seal component.

In another embodiment, the suspension liner includes an elongate, generally conical liner body formed from at least one material segment that is at least radially elastically extensible from a relaxed non-extended condition and including proximal and distal end areas, and a seal component connected to the liner body and having an exterior surface for engaging a prosthetic socket and at least one interior seal located along an interior surface of the seal component and arranged for engaging the liner body. A portion of the seal component carrying the interior seal extends freely and movable relative to the liner body.

The exterior seal may protrude from the exterior surface and extend radially outwardly from the seal component relative to a longitudinal axis of the liner body and opposite to the interior seal. The at least one interior seal can define at least one blade extending obliquely toward the liner body. The seal component may define a lip arranged against the liner body and the interior seal is located proximal relative to the lip.

In yet another embodiment, the suspension liner has an elongate, generally conical liner body formed from at least one material segment that is at least radially elastically extensible from a relaxed non-extended condition and including proximal and distal end areas, and a seal component connected to the liner body and having an exterior surface defining at least one exterior seal protruding from the exterior surface and extending radially outwardly from the seal component relative to a longitudinal axis of the liner body. The at least one interior seal is located along an interior surface of the seal component and defines at least one blade extending obliquely toward the liner body. A portion of the seal component carrying the interior seal extends freely and movable relative to the liner body.

According to any of the suspension liner embodiments having a seal embodiment, the seal component may be located at various locations along the exterior surface of the liner body relative to the proximal and distal ends. For example, a "high profile" suspension liner may have a seal component which is located 3-6 cm more proximally than a conventional suspension liner with a seal component. This particular configuration may be employed for those users that require a more proximal seal, particularly trans-tibial amputees. By locating the seal component more proximally relative to the liner body, a larger vacuum chamber is created distally of the seal component than in conventional suspension liners having a seal component. Moreover, the seal component may be located proximal from a sensitive distal end of the residual limb.

Any of the liner body embodiments described herein may define a circumferential recess arranged to receive a length of the seal component. The seal component may be fixedly secured to the liner without permitting adjustment of the location of the seal component relative to the liner body, or alternatively the seal component may be securable over any desirable location of the liner body by a clinician.

The liner body may have a variable thickness. In an exemplary embodiment, the liner body may have a significantly greater thickness at the distal end, and gradually taper toward the proximal end. In doing so, a circumferential recess of the liner body may define a reduced thickness region compared to regions adjacently outside the circumferential recess.

BRIEF DESCRIPTION OF THE DRAWINGS

The numerous other advantages, features and functions of embodiments of a suspension liner will become readily apparent and better understood in view of the following description and accompanying drawings. The following description is not intended to limit the scope of the suspension liner, but instead merely provides exemplary embodiments for ease of understanding.

It should be noted that the drawing figures are not necessarily drawn to scale, but instead are drawn to provide a better understanding of the components thereof, and are not intended to be limiting in scope, but rather to provide exemplary illustrations. It should further be noted that the figures illustrate exemplary configurations of a liner, and in no way limit the structures or configurations of a liner thereof according to the present disclosure.

DETAILED DESCRIPTION OF VARIOUS EMBODIMENTS

A better understanding of different embodiments of the invention may be had from the following description read in conjunction with the accompanying drawings in which like reference characters refer to like elements.

A. Overview of Suspension Liner Embodiments

In each of the embodiments discussed herein, the suspension liner is intended for use between a residual limb and a prosthesis, such as a hard socket, and to be airtight when donned over a residual stump. The internal surface of the liner may be formed of a layer of silicone elastomer, therefore serving as a skin interface. Silicone is advantageous in that it allows for different levels and softness and strength to be incorporated into the liners of the present application. Moreover, silicone permits the addition of selected supplements, such as petroleum jelly and aloe vera, which improve skin care and comfort.

An elasticity controlling matrix material may be provided on the exterior of the liner, the matrix material preferably being relatively compliant in a radial direction and substantially rigid or inelastic in an axial direction. The matrix material may extend over the distal or external side of the prosthesis, and is advantageous in that it prevents movement of the liner when a prosthesis is worn thereover.

A liner in accordance with this disclosure may be fabricated in a sufficient number of sizes to accommodate various sizes of residual limbs. In use, a liner of the type described herein is rolled up from the proximal to the distal end, placed over the distal end of the residual stump and rolled back up or "donned" over the stump like a stocking. This procedure and the benefits achieved thereby are described in detail in U.S. Pat. No. 4,923,474, granted on May 8, 1990 and incorporated herein by reference. In addition, any of the liners and sleeves mentioned herein may be constructed in the manner prescribed by U.S. Pat. No. 4,923,474.

The embodiments of the suspension liner of the present application may be constructed according to the molding methods described in U.S. Pat. No. 6,485,776, granted on Nov. 26, 2002 and the entirety of which is incorporated herein by reference.

B. Specific Embodiments of the Suspension Liner with a Seal Component

Figure 1:
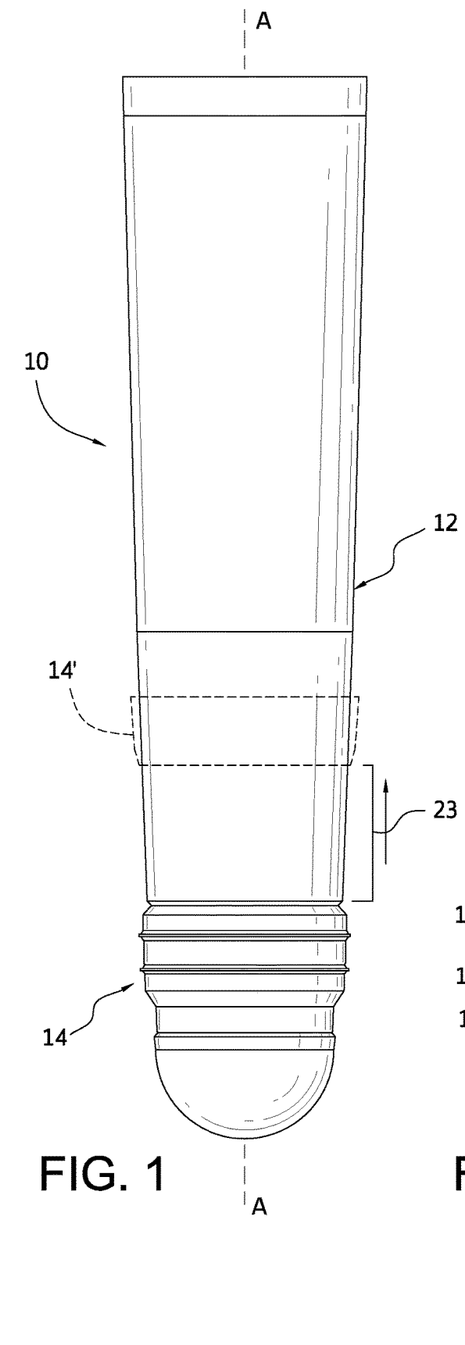
FIG. 1 is an elevational view of an embodiment of a suspension liner having a seal component.

FIG. 1 illustrates an embodiment of a suspension liner 10 in accordance with the invention. The liner 10 includes a liner body 12, and a seal component 14 connected to the liner body 12.

The liner body 12 preferably has an elongate, generally conical shape. The liner body 12 defines a longitudinal axis A-A, and includes proximal and distal end portions. The liner body 12 may be formed from at least one material segment that is at least radially elastically extensible from a relaxed non-extended condition.

Figure 2:
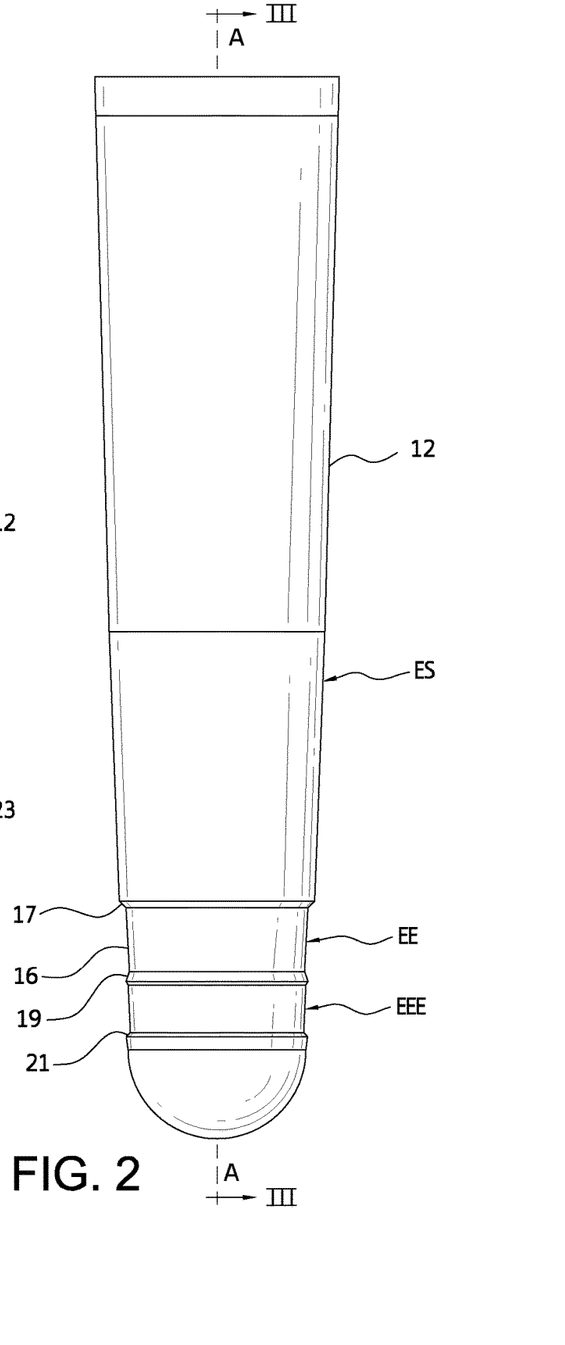
FIG. 2 is an elevational view of the suspension liner without the seal component.

As depicted in FIG. 2, the liner body 12 is preferably formed with a circumferential recess 16 for receiving the seal component. Particularly, the recess 16 compensates for the thickness of the seal component in such a manner that the seal component does not extend or substantially extend in excess or at all beyond an exterior surface ES of the liner body 12 located outside of regions of the recess 16. The seal component 14 may be secured against the exterior surface EE of the liner body located within the recess 16. Moreover, another exterior surface EEE located within the recess 16 is arranged for receiving a portion of the seal component, the base portion 20 described in FIGS. 4 and 5, defines an attachment portion that is adhered or otherwise fastened to the liner body 12.

The liner body 12 forms a proximal beveled circumferential edge 17 at a proximal end portion of the recess, a distal beveled edge 21 at a distal end portion of the recess, and a middle beveled circumferential edge 19 located between the proximal and distal end portions of the recess. The beveled edges receive portions of the seal component and minimize sharp or harsh edges that may cause discomfort when the residual limb is in a socket with the liner donned.

FIG. 1 generally shows the seal component 14 in a "conventional" location, however as also shown in FIG. 1, the seal component 14' can be located more proximal by a distance 23 relative to the liner body. For example, the seal component 14' may be located 3 to 6 cm more proximal than in the conventional location. This particular configuration may be employed for those users, particularly trans-tibial amputees that require a more proximal seal. By locating the seal component more proximal relative to the liner body, a larger vacuum chamber is created distally of the seal component than in conventional suspension liners having a seal component. Moreover, the seal component may be located proximal from a sensitive distal end of the residual limb.

The entire liner body 12 may be configured, including the recess 16, for the proximal seal component 14'.

Figure 3:
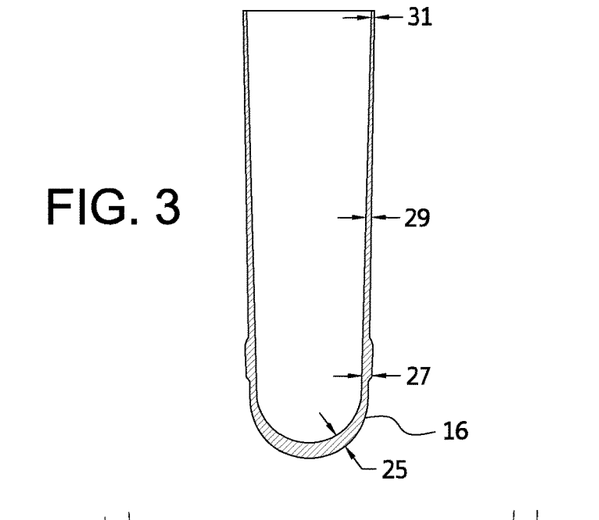
FIG. 3 is a cross-section view of the suspension liner according to FIG. 2.

FIG. 3 shows how the liner body may include a tapered thickness from the distal end to the proximal end. For example, the distal end may have a thickness 25 of 12-15 mm and taper in thickness 27 of 6-8 mm distally adjacent the recess 16. The thickness 29 proximally adjacent the recess 16 may be 4-6 mm with the thickness 31 tapering to the proximal end to a thickness around 2.0-3.0 mm. The thickness of the liner provides additional cushioning at the distal end, and easy roll-on/off at the proximal end when the liner is donned or doffed. Additional thickness is about the recess to accommodate the seal component.

Figure 4:
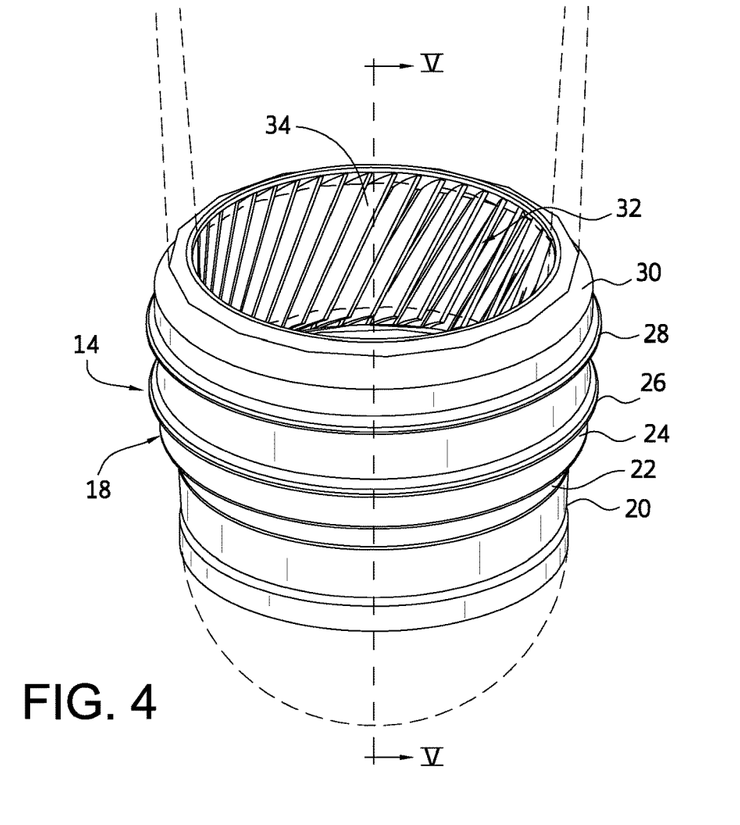
FIG. 4 is a schematic view showing the seal component according to FIG. 1.
Figure 5:
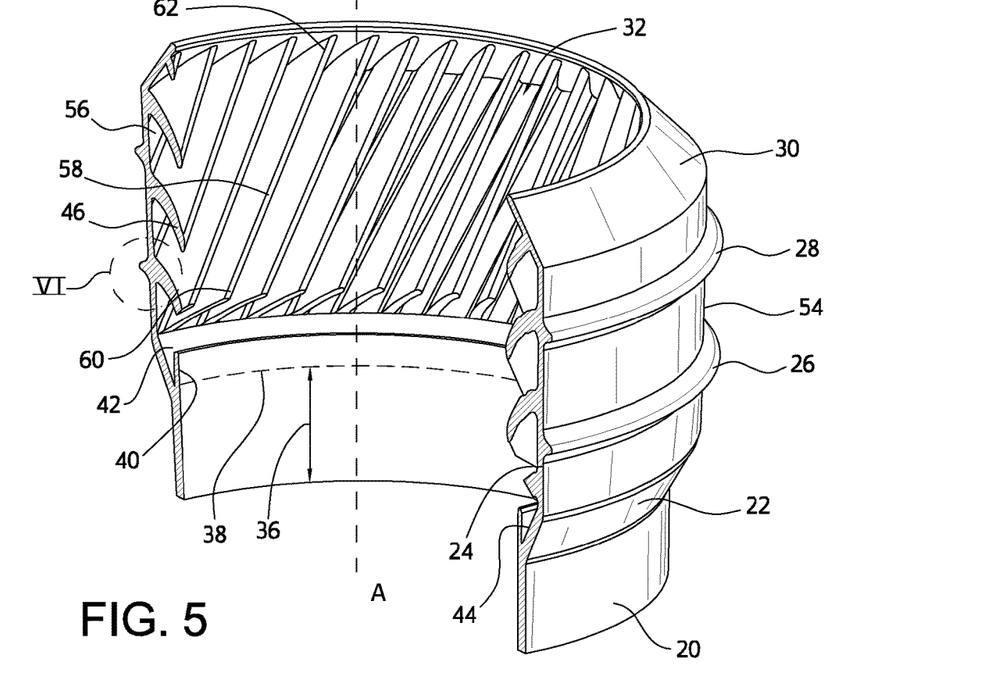
FIG. 5 is a cross-section view of the seal component of FIG. 4 taken along line V-V.

In an exemplary embodiment, FIGS. 4 and 5 show a seal component 14 having both exterior and interior configurations 18, 32. The exterior configuration 18 is arranged for engaging against a prosthetic socket wall, whereas the interior configuration is arranged for engaging the exterior surface ES of the liner body 12.

The seal component 14 includes a base portion 20 located at the distal portion of the seal component, and secures to the exterior surface EE of the recess 16. An interior surface 36 of the base portion 20 is preferably anchored circumferentially to the exterior surface EE to a pivot line 38. A seal wall 22 is located above the pivot line 38, and flexibly and movably extends relative to the liner body 12 and the base portion 20.

The seal component 14 defines a lip 40 which extends above the base portion 20 and parallel to the exterior surface EE of the liner body 12. The lip 40 is adhered to the liner exterior surface EE, and provides additional retention of the seal component to the liner body. The lip may be tapered so as to provide a gradual transition along the liner body.

A gap 42 is formed between the lip 40 and a surface 44 of a distal outwardly pitched portion 22 of the seal wall 24. The gap 42 enables the seal wall 24 to flexibly and movably extend relative to the liner body. The distal outwardly pitched portion 22 effectively forms a taper for the seal component in order to facilitate donning of the suspension liner in a prosthetic socket.

The seal wall 24 has exterior and interior surfaces 54, 56, corresponding respectively to the exterior and interior configurations 18, 32. The exterior surface 54 carries a plurality of individual exterior radially extending seal rings 26, 28. These seal rings 26, 28 are arranged to engage the interior socket wall, and expel air through a valve on the socket as the residual limb carrying the liner is stepped into the socket. The seal rings form an airtight connection between the liner and the socket, and ensure secure suspension.

While two seal rings are shown in FIG. 4, the seal component may have either one or any number of seal rings as considered necessary to form an airtight connection with a socket.

Figure 6:
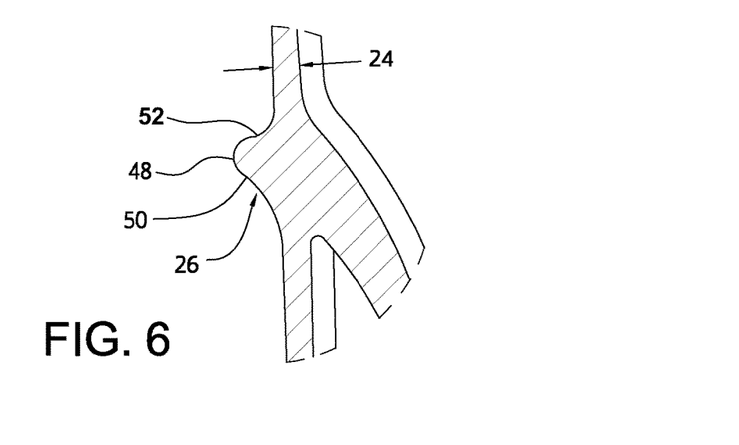
FIG. 6 is a sectional view corresponding to detail VI in FIG. 5.
Figure 7A:
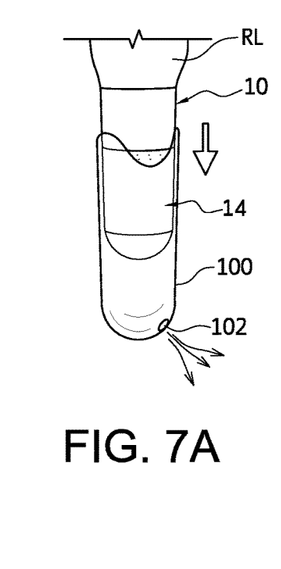
FIGS. 7A-7E are schematic views showing the donning and doffing of the suspension liner with a prosthetic socket.
Figure 7B:
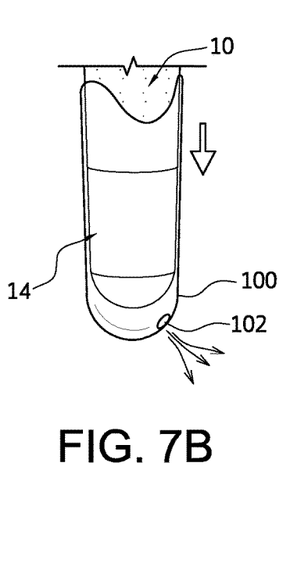
Figure 7C:
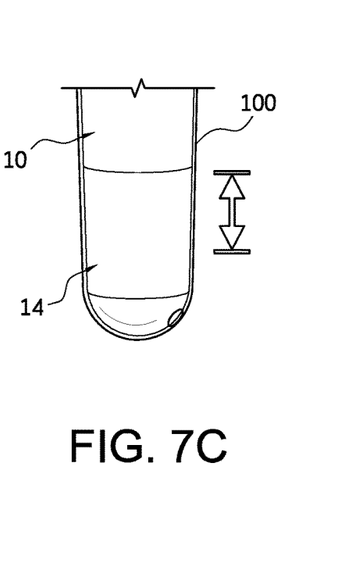
Figure 7D:
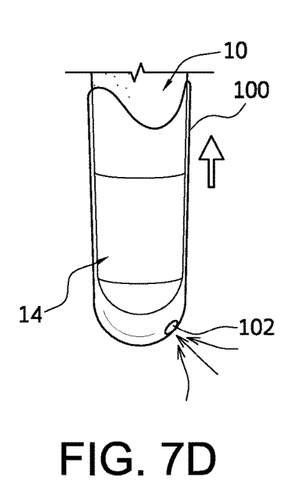
Figure 7E:
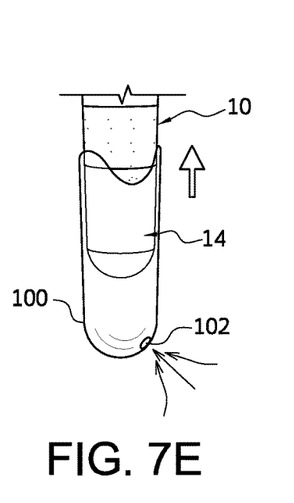

According to FIG. 6, each of the seal rings 26, 28 includes a distal pitched section 50, a proximal pitched section 52, and a peak 48 located therebetween. It will be understood that the seal rings may take any number of configurations, and are not limited to the variation depicted in FIG. 5. Indeed, the seal rings may be construed in the manner of any one of the seal rings depicted and discussed in U.S. Pat. No. 8,304,120. For example, the pitched sections may have either a linear, cross-sectional profile, or a curved, cross-sectional profile. Further yet, the seal rings may take a variety of other cross-section profiles such as in the form of a square or with rounded edges.

According to FIG. 5, the interior configuration 32 is formed along the interior surface 56 of the seal wall 24, and is bounded by the distal outwardly pitched portion 22 and a proximal inwardly pitched portion 30 located at the uppermost end of the seal component 14. As with the outwardly pitched portion 22, the inwardly pitched portion 30 acts as a transition to facilitate donning and doffing of the liner in a socket.

A plurality of blades 34 are located along the interior surface 56 of the seal wall 24, and the plurality of blades 34 extend circumferentially about the seal wall 24. The blades compensate for volume changes in the residual limb, by expanding and exerting pressure against an interior surface of the socket so as to improve suspension of the liner over known suspension liners with seals.

In the depicted embodiment of FIG. 5, the blade has a smallest width (direction of interior surface of seal wall toward the liner body) at a distal portion 60, and gradually increases across a central portion 58 to a proximal portion

62. The taper allows for a smooth transition of the interior seal to the distal and proximal end portions, thereby avoiding any sharp edges and avoiding any pressure points that may cause discomfort to the residual limb.

The arrangement of the blade width may include other variations such as the width of each of the blades tapering from a central portion 58 to a distal portion 60, and likewise from the central portion 58 to a proximal portion 62. In another variation, the blade width may be substantially uniform from distal to proximal portions.

Each blade has a greatest thickness closest to the interior surface 56 of the seal wall with a tapered thickness 46 as the blade extends toward the liner body. This configuration strengthens the blade at its interface with the seal wall as well as reduces any possible pressure points.

In the variation shown in FIG. 5, each of the blades is arranged at an oblique angle relative to the longitudinal axis A-A of the liner. This arrangement permits the blades to expand outwardly as the liner is donned onto the residual limb and fold down toward the seal wall with some overlap over each of the blades as the liner is doffed. The blades are also arranged at an angle so as to ensure that each blade folds in a proper predetermined direction so as to avoid the creation of any pressure points.

According to one variation, the blades extend at an angle approximately at 27 degrees relative to the longitudinal axis of the liner body. This angle, among other angles as well, allows for the blades to be pressed inwards relative to the liner body when the liner is donned, and obtains a proper balance of force required to draw the blades outwardly when the liner is withdrawn from the socket. Because the angle of the blades is arranged relative to the vertical axis of the liner and is combined with the orientation of the ends of the blades which press against the liner body, when a force is exerted to pull the liner out of a socket, the blades expand outwardly, which in turn creates extra pressure of the seal wall against the socket wall, thereby making it more difficult to lose suspension of the liner.

It will be noted that the blades are not limited to an obliquely extending configuration, as explained in connection with FIG. 4, but the blades may be arranged in any number of configurations such as being either generally parallel or perpendicular relative to the longitudinal axis A-A of the liner.

The seal component is preferably formed as a separate element from the liner body, and is securely attached thereto by appropriate bonding techniques that may include adhesive, heat seal, etc. The seal component may be constructed from a variety of materials, such as polymers, rubbers, coated textiles or any other suitable material. According to the embodiments, the seal component is constructed from a silicone composition.

While the seal component is described and depicted at the distal end portion of the liner, the seal component may be placed at any particular location along the exterior surface ES of the liner body.

Turning to FIGS. 7A-7E, the liner 10 carrying the seal component 14 is shown worn on a residual limb RL and stepped into a prosthetic socket 100. As the residual limb RL is placed into the socket 100, the seal component 14 forms an airtight seal with an interior surface of the socket 100 and urges air out of the distal end of the socket through a distally positioned expulsion valve 102. When it is desired to release the connection between the liner and the socket, the valve is released, and the residual limb can be removed from the socket.

When sealing against a socket, it should be kept in mind that the vacuum is formed between the seal and the distal end of the socket; no vacuum is created proximal of the socket between the liner and the socket. Moreover, the seal does not completely press against the socket wall, in that only portions of the seal press against the socket wall. For example, the seal rings press against the socket wall, but portions between the seal rings may not, and further may not touch the socket wall. Moreover, gaps between the blades may affect areas of the seal so that at such areas the seal does not exert any or much pressure against the socket wall.

Figure 8:
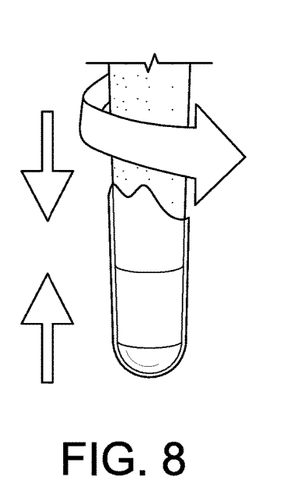
FIG. 8 is a schematic view showing minimization of the movement of the residual limb in a socket.

As shown in FIG. 8, the pressure is inversely proportional to the suspension force needed, so as to ensure stability and rotational control. The seal component 14 forms a hypobaric sealing membrane that conforms to the shape of the internal socket wall, providing an airtight seal between the suspension liner and the socket. The recess in the liner body allows for there to be even pressure around the seal in the connection between the socket and liner. There is firm suspension, through the usage of the blades, to accommodate volume fluctuations of the residual limb.

Of course, it should be understood that not necessarily all objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

The skilled artisan will recognize the interchangeability of various disclosed features. In addition to the variations described herein, other known equivalents for each feature can be mixed and matched by one of ordinary skill in this art to construct suspension liners in accordance with principles of the present invention.

Although this invention has been disclosed in the context of certain exemplary embodiments and variations thereof, it therefore will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above.

The invention claimed is:

1. A liner for providing an interface between a residual limb and a prosthetic socket, comprising:
   an elongate, generally conical liner body being radially elastically extensible and including proximal and distal end areas, the liner body having an exterior surface and defining a longitudinal axis defined between the proximal and distal end areas;
   the liner body formed with a circumferential recess defining first and second exterior surfaces within the recess and axially separated from one another by a circumferential edge;
   a seal component located within the circumferential recess;
   wherein the seal component defines a base portion secured to the second exterior surface of the recess;
   wherein an interior surface of the base portion is anchored circumferentially to the second exterior surface;
   wherein the interior surface of the base portion extends to a pivot line defined by the seal component, a lip extends above the base portion and is parallel to the first exterior surface of the circumferential recess.

2. The liner of claim 1, wherein the lip is adhered to the first exterior surface of the circumferential recess.

3. The liner of claim 1, wherein the lip is tapered to provide a gradual transition along the first exterior surface of the circumferential recess.

4. The liner of claim 1, wherein a seal wall is located above the pivot line, and flexibly and movably extends relative to the first exterior surface of the circumferential recess and the base portion.

5. The liner of claim 1, wherein a seal wall has exterior and interior surfaces extending from the base portion from a distal outwardly pitched portion directed away from the first exterior surface, the seal wall forms a gap from the outwardly pitched portion in that the interior surface of the seal wall is spaced a distance from the first exterior surface of the circumferential recess.

6. The liner of claim 5, wherein the seal wall has a proximal inwardly pitched portion located at an uppermost end of the seal component and directed to the first exterior surface.

7. The liner of claim 1, wherein the circumferential recess is bounded by at least one of a proximal beveled circumferential edge at a proximal end portion of the circumferential recess or a distal beveled edge at a distal end portion of the circumferential recess.

8. The liner of claim 1, wherein the circumferential recess is arranged to compensate for a thickness of the seal component in such a manner that the seal component does not extend or substantially extend in excess or at all beyond an exterior surface of the liner body located outside of regions of the circumferential recess.

9. The liner of claim 1, wherein the seal component includes at least one exterior configuration defined along an exterior surface of the seal component and protrudes radially outwardly from the seal component relative to the longitudinal axis of the liner body to form a ring.

10. A method for securing a prosthetic socket to a liner for providing an interface between a residual limb and the prosthetic socket, the liner having an elongate, generally conical liner body being radially elastically extensible and including proximal and distal end areas, the liner body having an exterior surface and defining a longitudinal axis defined between the proximal and distal end areas, the liner body formed with a circumferential recess and a seal component located within the circumferential recess, the method comprising the steps of:

providing the seal component with an exterior surface for engaging the prosthetic socket and at least one interior seal located along an interior surface of the seal component and arranged for engaging an exterior surface of the liner body within the circumferential recess, the interior seal extending freely and movable relative to the liner body, the seal component includes a base portion located at the distal portion of the seal component and below the at least one interior seal, the base portion securing to the exterior surface of the liner body within the circumferential recess;

placing the liner within the prosthetic socket and forming an airtight seal with an interior surface of the socket and the seal component;

urging air from a distal end of the prosthetic socket such that a vacuum is formed between the seal component and the distal end of the prosthetic socket;

wherein the at least one interior seal defines at least two blades having a gap therebetween such that the seal component intermittently applies pressure between the exterior surface of the circumferential recess and the interior surface of the prosthetic socket.

11. The method of claim 10, wherein no vacuum is created between the liner and the prosthetic socket proximally from the seal component.

12. The method of claim 11, wherein the seal component defines at least one exterior seal protruding from the exterior surface and extending radially outwardly from the seal component relative to a longitudinal axis of the liner body and opposite to the interior seal.

13. The method of claim 12, wherein only the at least one exterior seal presses against the interior surface of the prosthetic socket from the seal component.

14. The method of claim 10, wherein the at least one interior seal defines at least one blade extending toward the liner body obliquely relative to the longitudinal axis.

15. The method of claim 13, wherein the seal component defines a lip arranged against the liner body, the at least one interior seal being located proximal relative to and above the lip.

16. The method of claim 10, comprising the steps of:
forming a hypobaric sealing membrane by the seal component conforming to a shape of an internal wall of the prosthetic socket to form an airtight seal between the liner and the prosthetic socket;
forming even pressure around the seal component such that the seal component is pressed and generally contained within the circumferential recess between the socket and liner.

* * * * *